(12) United States Patent
Allburn (10) Patent No.: US 8,666,131 B2
(45) Date of Patent: Mar. 4, 2014

(54) BIOMETRIC SELF-CAPTURE CRITERIA, METHODOLOGIES, AND SYSTEMS

(76) Inventor: David Allburn, Glouster, OH (US)

( * ) Notice: Subject to any disclaimer, the term of this patent is extended or adjusted under 35 U.S.C. 154(b) by 119 days.

(21) Appl. No.: 13/222,360

(22) Filed: Aug. 31, 2011

(65) Prior Publication Data

US 2011/0311111 A1 Dec. 22, 2011

Related U.S. Application Data (63) Continuation-in-part of application No. 12/188,506, filed on Aug. 8, 2008, now Pat. No. 8,398,118.

(60) Provisional application No. 61/002,770, filed on May 15, 2008, provisional application No. 61/379,211, filed on Sep. 1, 2010.

(51) Int. Cl.
*G06K 9/00* (2006.01)

(52) U.S. Cl.
USPC ......................................................... 382/128

(58) Field of Classification Search
None
See application file for complete search history.

(56) References Cited

U.S. PATENT DOCUMENTS

| | | | |
|---|---|---|---|
| 5,381,487 A * | 1/1995 | Shamos ........................ | 382/115 |
| 8,077,934 B2 * | 12/2011 | Fenrich et al. ................ | 382/124 |
| 8,274,594 B2 * | 9/2012 | Hsu et al. ...................... | 348/340 |
| 2003/0169334 A1 * | 9/2003 | Braithwaite et al. ............ | 348/78 |
| 2004/0032975 A1 * | 2/2004 | Boccacci ....................... | 382/115 |
| 2005/0129293 A1 * | 6/2005 | Acharya et al. ................ | 382/125 |
| 2008/0012850 A1 * | 1/2008 | Keating, III ................... | 345/419 |

\* cited by examiner

*Primary Examiner* — Nancy Bitar (74) *Attorney, Agent, or Firm* — Porter, Wright, Morris & Arthur, LLP (57) ABSTRACT

A system for capturing specified biometric self-capture specimens to create a record used for verification comprising a processor, scanner, printer, and secure database. The processor is programmed to 1) activate the scanner to create a digital image of the biometric self-capture specimens in a uniquely flexible predetermined format, 2) link the image to information assigned to the specimens, 3) assign a score to individual components of the image based on quality according to a standard for that component, 4) display the score to a user, 5) retain the components with the highest scores, 6) arrange the retained components and the linked information in the predetermined format to create a record, active the printer to print the record either as an electronic file or a paper file, and 7) transmit the electronic file to a secure database in a secure manner.

18 Claims, 7 Drawing Sheets

BIOMETRIC SELF-CAPTURE CRITERIA, METHODOLOGIES, AND SYSTEMS

CROSS-REFERENCES TO RELATED APPLICATIONS

The present application claims the benefit of U.S. provisional application 61/379,211 filed Sep. 1, 2010 and is a continuation in part of U.S. patent application Ser. No. 12/188,506, filed Aug. 8, 2008, which claims the benefit of U.S. provisional application No. 61/002,770 filed Nov. 13, 2007, each of which is hereby incorporated by reference in its entirety.

FIELD OF THE INVENTION

The present invention relates generally to biometric self capture systems and specifically to solutions used to capture specific biometric specimens in a specific way and to record, coordinate, validate and transmit data derived from and depicting the biometric self-capture specimens.

BACKGROUND OF THE INVENTION

Biometric specimens are unique biological information about a certain person. Biometric Self-capture (BioSc) is a process in which a willing individual (Subject) enables acquisition (Capture) of eligible personal biometric specimens:
  For all of certain beneficial purposes,
  Using all of certain facilitating acquisition methodology,
  Using all of certain facilitating acquisition circumstances, to
  Produce specimens of certain authenticity, quality and longevity.

Biometric specimens found eligible or made eligible for BioSc reduce their cost-of-acquisition, increase their authenticity, thus acquire unique added value and utility for society and business. Eligibility of a biometric specimen for BioSc is achieved by meeting all of the following listed purposes, by using all the listed acquisition methodology in all the listed circumstances, to achieve sufficient documented specimen authenticity, quality, and longevity.
  Beneficial Purposes:
  Other than law-enforcement purposes.
  Other than medical diagnostic purposes.
  Such as (exemplary) identification or background screening purposes.
  Methodology for facilitating the acquisition of BioSc specimens includes:
    1. Capture that occurs only by the Subject's own physical effort.
    2. Capture that does not require another's touching of the Subject's body or garments.
    3. Capture that does not require use of electronic or high value technological apparatus.
    4. Capture that produces multiple specimens of quality sufficient for their purpose.
  Circumstances under which BioSc specimens are acquired include:
    1. All steps of Capture are always observed by a registered trusted observer present (RTO).
    2. All specimens are collected by the RTO, establishing a credible chain of custody.
    3. Capture and observation can occur in public as well as private locations without violating social privacy and religious norms adhered-to by the Subject.

BioSc specimens Captured under the conditions listed above produces:
  1. Specimens of sufficient quality for their intended purpose.
  2. Specimens that endure fifteen years of room temperature storage.

Biometric specimens found or made eligible for self-capture are specimens that meet the purposes, methodology, circumstances, and quality criteria. Examples include fingerprints, palm prints, tooth bite impressions, cheek-swab DNA, saliva, scent, hair, any written list of direct linear measurements, hand-sketches, worded descriptions, descriptive locations of tattoos, piercings, and other unique body observables such as missing appendages. Bodily fluids Captured for forensic purposes are eligible if privacy and religious norms allow an RTO to witness production of the specimens, and if the specimens can be preserved as specified.

in an embodiment, biometric specimens found ineligible for self-capture under the present invention are those that are excluded for failure to meet the methodology or purpose criteria. Specifically excluded are those specimens that exclusively require use of electronic or advanced equipment for Capture, or those that are Captured for medical evaluation or diagnosis or law enforcement. Advanced equipment is any Capture mechanism that utilizes electronic or photographic apparatus such as a sound recorder or a camera. Specifically excluded are those specimens whose purpose for Capture is for medical diagnosis such as bodily fluids and tissues, gait, neural reflexes, smell, and blood perfusion time. Also specifically excluded are specimens whose purpose for capture is in connection with an arrest booking or criminal charges. A hair sample would be eligible for BioSc if Capture is witnessed for the purpose of detecting recent use of illegal substances pursuant to employment eligibility. A hair sample would be ineligible for BioSc if Captured for the medical purpose of determining a course of treatment for addiction to illegal substances or for determining violation of parole. Thus, the eligibility of a specimen for BioSc is determined by the actual purpose at hand, not by the variety of possible purposes imaginable.

For economic and quality assurance reasons, efficient and cost-effective methods to identify, track and submit BioSc Captured specimens to agencies are desirable. Digital representation of BioSc Captured specimens is necessary for efficiently linking stored specimen data to submitted specimen data. A system is needed to protect specimens and their derived or accompanying data from theft or abuse. A system is needed that provides confidence in the authentication process. A system is needed that provides an electronic or physical chain of custody for the BioSc Captured specimens.

The present invention addresses the above-described problems by providing a fast, efficient, accurate, and automatic method of capturing biometric self capture specimens and recording, coordinating, validating and transmitting biometric self-capture data therefrom.

BRIEF DESCRIPTION OF THE INVENTION

The present invention is a method of Capturing BioSc specimens to create a record used for verification. The system comprises a processor interconnected to a scanner, a printer, and a secure database. The processor is programmed to 1) activate the scanner to create a digital image of the biometric self-capture specimens in a uniquely flexible predetermined format, 2) link the image to information stored in a memory of the processor, the information assigned to the specimens, 3) assign a score to individual components of the image based on quality according to a standard for that component, 4) display the score to a user, 5) retain the components with the highest scores, 6) arrange the retained components and the linked information in the predetermined format to create a record, activate the printer to print the record either as an electronic file or a paper file, and 7) transmit the electronic file to a secure database in a secure manner. The specimen (or specimens in a multiple capture kit) is one or more specific identifier, such as a set of fingerprints, a palm print, a tooth bite impression, a cheek-swab DNA, saliva, scent, hair, a written list of direct linear measurements, a hand-sketch, a worded description of physical features, a description of a tattoo and a tattoo body part location, a body part piercing, a missing appendage, and the like.

In an embodiment, security is provided by a connection layer with multiple channels that simultaneously transfer data. In an embodiment, the electronic file is transmitted to the secure database via a channeler, encrypted and transmitted through a connection layer with multiple channels that simultaneously transfer data. The transmission is encrypted and the record is transmitted by parsing Personally Identifiable Information (PII) from the images of the biometric specimens and parsing out key identifiers such as, but not limited to social security number, date of birth, driver's license number, vehicle registration plate number, credit card numbers, birthday, birthplace, and the like.

The recipient has a reception module having a decryption element that receives the encrypted parsed record and reassembles it using a common key. In an embodiment, the common key is a barcode number, RFID tag, watermark, and the like. The record is reassembled at the recipient only after the parsed information is inside the recipient's security layer. Integrity verifiers are used to ensure that the record is reassembled intact.

In an embodiment, the present invention comprises A processor interconnected to a scanner, a printer, and a secure database, the processor programmed to 1) activate the scanner to create a digital image of the biometric self-capture specimens in a multi-page predetermined format, 2) link the image to information stored in a memory of the processor, the information assigned to the specimens, 3) enhance the imagery using proprietary algorithms from the technologies of military reconnaissance and astronomy to assign a score to individual components of the image based on quality according to a standard for that component, 4) display the score to a user, 5) retain the components with the highest scores, 6) arrange the retained components and the linked information in the predetermined format to create a record, activate the printer to print the record either as an electronic file or a paper file, and 7) transmit the electronic file to a secure database.

In an embodiment, the present invention comprises a system combining the attributes, criteria, purposes, and circumstances that make certain biometric specimens eligible to be conveniently produced with high forensic quality by claimed ergonomic methodology that is superior to prior art, together described as Biometric Self-capture. In an embodiment, the present invention employs sophisticated methods to enhance and select the best quality specimens from the many resulting from Biometric Self-capture and format such best-of-breed specimens according to various agency specifications to support digital query of agency databases for matching with like specimens stored for a socially beneficial purpose. In an embodiment, the present invention comprises individual subroutines, linkages, anti-fraud, security, privacy, and procedural details that embody an exemplary system of Biometric Self-capture applied to non-criminal applicant fingerprinting.

As used herein, "approximately" means within plus or minus 25% of the term it qualifies. The term "about" means between ½ and 2 times the term it qualifies.

The methods of the present invention can comprise, consist of, or consist essentially of the essential elements and limitations of the invention described herein, as well as any additional or optional ingredients, components, or limitations described herein or otherwise useful in compositions and methods of the general type as described herein.

All references to singular characteristics or limitations of the present invention shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

DETAILED DESCRIPTION OF THE INVENTION

The present invention provides systems and components thereof, for capturing biometric self-capture specimens and deriving, recording, coordinating, validating and transmitting compiled data depicting said specimens in any form including digital, and related demographic information. The systems provided by the invention provide flexibility, quality, economy, and/or convenience superior to present systems. Flexibility means that the system can be used with a variety of eligible specimens and unlike current art, can capture specimens simultaneously from seated groups of persons. Quality means that specimen(s) that meet defined standards are selected from multiple specimens. Economy means BioSc specimens are to be collected easily and at low costs.

Convenience means that the systems embodying this invention can be used in multiple different ad hoc venues such as residences, restaurants, hotel meeting rooms, small branch offices of businesses, and remote villages of undeveloped countries lacking electrical power and literate Subjects. Convenience additionally means systems provided by the invention can Capture specimens from persons who can neither read nor write, and from persons who speak languages not spoken by the RTO.

The present invention comprises a system to acquire, authenticate and use biometrics otherwise eligible for BioSc. Advantages of the present invention include:

Biometric sampling methodology distributed in convenient packaging.

Registered Trusted Observer (RTO) establishment, qualifying, recruitment, training, and deployment methods for Chain-of-custody.

Processing and digitizing methods applied to the biometric specimens.

Data Privacy Protection (DPP) methods.

Scalable system architecture adjustable to local or international projects.

Accommodation of intended Subjects' religious and social traditions.

Figure 1:
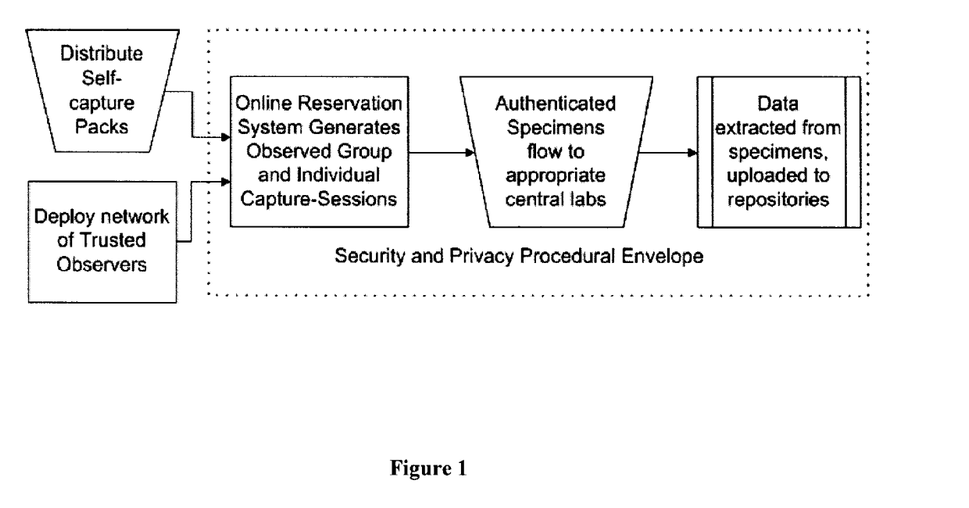
FIG. 1 is flow chart of an embodiment of the invention.

As shown in FIG. 1, the present invention is a system that distributes BioSc self-capture packs (alternately, "kits") to a location having an RTO on hand. The system includes a reservation system that identifies the self-capture packs distributed to a particular RTO. After Capture, the specimens are securely transmitted to approved laboratories for data extraction and electronic record formation. The records created are then transmitted to be verified, stored, matched, or otherwise processed by designated agencies with results distributed to the authorized requestor.

One of the present invention's unique advantages is the sole use of biometrics that are eligible for BioSc. In an embodiment, the disposable kit (US patent application 20090285458 filed Nov. 19, 2009; the Self-capture™ Pack from National Fingerprint, Inc.) that captures forensic quality multifold print impressions of fingers and optionally the palm, while meeting all the eligibility criteria for BioSc, serves as the basis for the present invention. This embodiment meets one or more of the needs listed below to benefit the public by increasing safety, decreasing fraud, preventing crime, and other non-medical diagnostic purposes.

Criminal history retrieval in support of pre-employment background screening.

Enrollment for fraud-resistant voter registration and social services distribution.

Enrollment with cell phone purchase for crime prevention and solving.

Census-taking.

Other classes of contingent identification (such as ante mortem data).

in an embodiment, the present invention comprises the sequence of events beginning with a request and distribution of a kit or packet, and concluding with the disposition of the specimens and the data derived from them. The system comprises certain performance features in the capture of eligible specimens, including:

1. short time-to-capture of multiple specimens,
2. zero advance training of the Subject,
3. zero electric utility power at the capture site,
4. zero required literacy of the Subject,
5. facilitates simultaneous (parallel) group capturing,
6. requires no high-value or electronic apparatus to capture specimens,
7. deployable in kit form with at least three-years of shelf life,
8. produces long-lived, non-hazardous biometric specimens that ship or mail routinely,
9. amenable to return of specimens in archival form to the Subject or designee,
10. short time-to-train/deploy ubiquitous/mobile RTOs,
11. ease of on-site authentication,
12. high integrity, recorded and traceable chain-of-custody,
13. handling of specimens/data accommodates multi-layer privacy and security protection,
14. amenable to economic high volume central processing into digital form for upload,
15. upload formats/protocols meet specified governmental repository requirements, and
16. embodiment scales/adapts easily across differing social systems and countries.

The present invention provides for the discreet disposition of the specimens, ranging from documented destruction to receipted return of the specimens to a designated recipient in a specified form.

Figure 2:
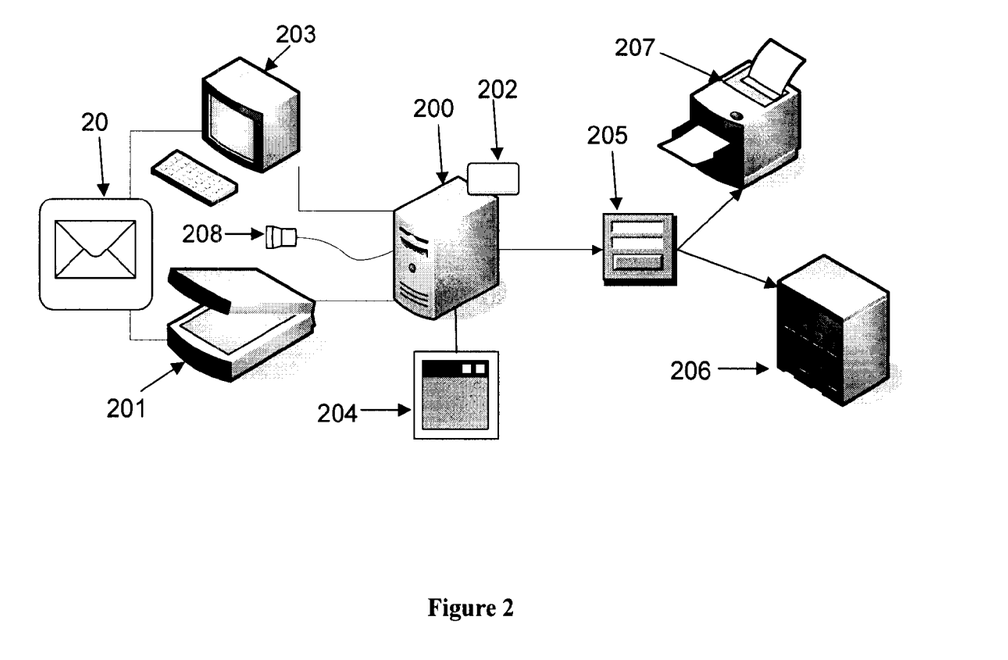
FIG. 2 is schematic of components of an embodiment of the invention.

As depicted in the embodiment shown in FIG. 2, the system comprises a computer 200, at least one approved scanner 201, software 202, The software 202 comprises an operating or embedded system designed to perform necessary processing functions, a suite of agency (such as FBI) approved modules, and the like. The software 202 includes a fingerprint processing store-and-forward module or modules, either custom-developed or purchased, which must be approved by the USA National Institute of Standards and Technology and the Federal Bureau of Investigation, or by similar international agencies.

Figure 3:
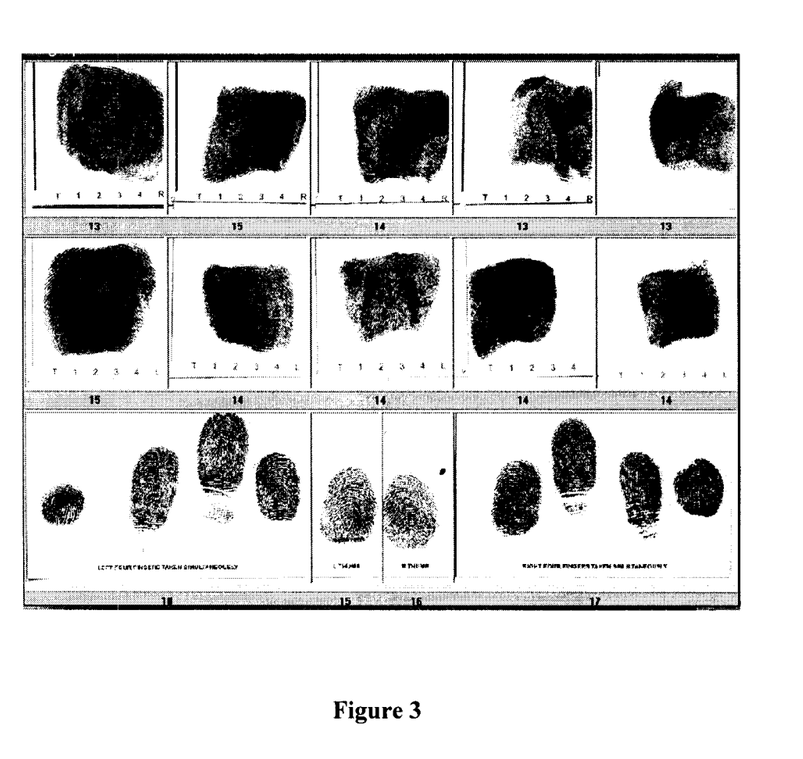
FIG. 3 is an embodiment of a scoring component of the invention.

The software of the system performs, among others, the following functions:

1. Operates the scanner to fetch an image of the BioSc specimen 20 and the scanner model identification numbers.
2. Carves-up the geometry of that image into demographic data fields and specific biometric specimen data (such as a fingerprint) areas. In an example using fingerprint data, 10 rolled images and 4 flat images comprise the image as illustrated in FIG. 3.)
3. Removes artifacts like unwanted lines, little rows of numbers, traps-out colored alignment marks, etc.
4. Magnifies and displays the demographic image area and offers a form for operator key-entry or optical character recognition (via a monitor input device 203) of those data items.
5. Detects and corrects misalignment such as to rotate each image (such as an individual fingerprint) to be exactly right-side-up.
6. Expands the size of each image to fill the allowed image area.
7. Optimizes and standardizes the exposure settings of each of the specimen images (for example, 14 chosen fingerprints). The system applies image enhancement techniques to extract and emphasize otherwise imperceptible ridge detail from apparently totally blacked-out or faint areas and to overcome known artifacts such as "Ghosting" or multiple imaging, to yield useable detail after such processing.
8. Scores the image quality of each of the images (for example, 14 prints) according to a standard for that image, and displays those scores in a usable way. The standard in this function is a quality standard from a requiring agency, such as the FBI (for example, whether the FBI will reject the record for low quality). The system of the present invention offers smooth adjustability of the scoring on a scale from "tough" to "lenient". As shown in FIG. 3, a color is assigned to each image to indicate the score (for example, as a bar under the image. Here, green indicates a score for that specimen is high; red indicates an image that could be rejected based on the agency standard).
9. Re-scans the image and retains the best images. This feature allows scanning of additional images (such as those use for practicing, etc.), comparing the score of each new image against the score of its previous counterpart, and keeping for display the higher scoring of the two.

10. Segments the images by evaluating whether (or how well) each original image matches a corresponding image. Segmentation provides assurance that each location for a flat image and each location for its corresponding rolled image contain an image that is "X % likely" to be made from the same exact body part (for example, a finger). If the images do not match, the software provides a message (such as "Left middle doesn't match)". The system of the present invention inter-compares all the rolled images with each other, and reports if there are any duplicates. It diagnoses likely "wrong positionings" and provides messages as to recommendations for correcting perceived errors. This feature facilitates a physical or virtual paste-up process. Again referencing the embodiment in FIG. 3, if a score is high, but the bar is colored red, a flag appears connected to a dialog box that explains a problem and suggests corrections. Single, as well as multiple different instances are part of the invention.

11. Prepares the entire record layout according to a detailed specification published by the appropriate agency (for example: Destination Automated Fingerprint Identification System (AFIS); Department of Law Enforcement (DLE), Division of Criminal Justice Information Services (CJIS); Volunteer & Employee Criminal History System (VECHS).

Figure 4:
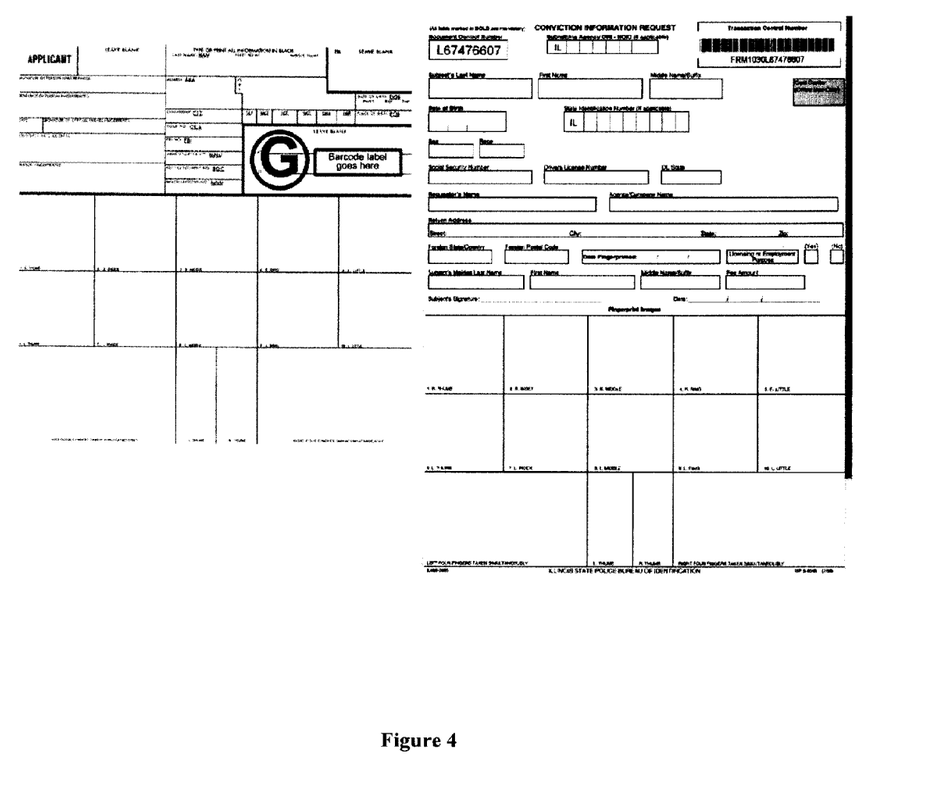
FIG. 4 is an embodiment of a record created in an embodiment of the invention.

12. Adjusts the layout and juxtapositions the demographics area, adding or blanking certain fields as the related specifications require. For example fingerprint cards destined for or supplied by, Financial Industry Regulatory Authority (FINRA), Office of Personnel Management (OPM), Royal Canadian Mounted Police (RCMP), etc., differ as to number, relative position, or syntax for demographic field content. As shown in the example in FIG. 4, the card on the right is a pre-barcoded Illinois fingerprint card prepared by the system. The card on the left is an FBI card prepared by the system which is made specific to FINRA by addition of a FINRA-supplied barcode which said software withdraws from a stored table of pre-issued codes.

13. Composes a "mock-up" 205 in memory of an image of the entire card, (refer again to FIG. 4) including the key-entered data fields arranged and populated as required by the requestor.

14. Adds agency (such as FBI) required details and transmits the data to a print image file that produces a perfected hard card with signature-on-file.

Figure 6:
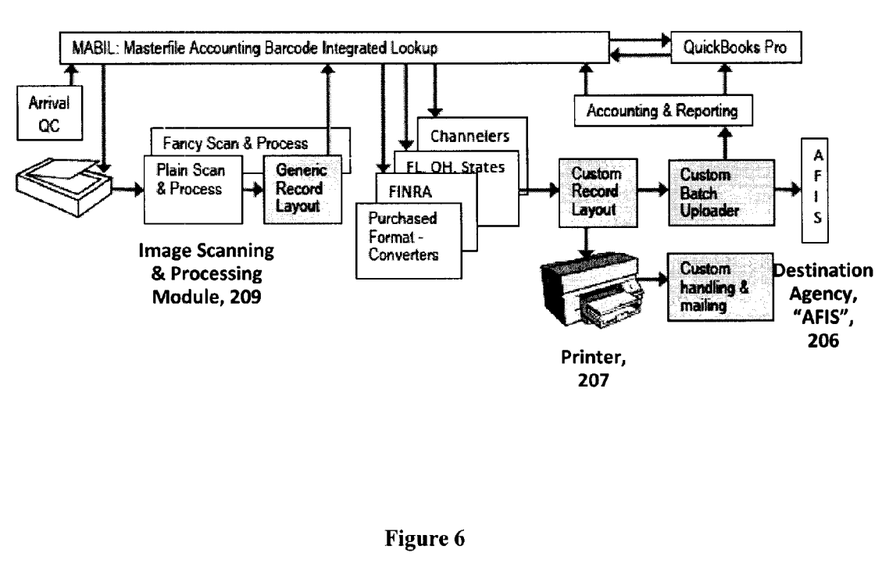
FIG. 6 is a schematic diagram of the capture and processing modules of the invention.

15. Utilizes an approved printer 207 (for example, an FBI-approved B&W laser printer as illustrated in FIG. 6) to produce as many duplicate cards for mailing (such as for FINRA or states). The printer either makes the entire card, or fills-in forms.

16. Connects electronically to an agency 206 (illustrated by block marked "AFIS" in FIG. 6) and transmits the data to a secure database.

The system eliminates the need for manual selection of the best quality images (such as prints), and for manually pasting of the physical fingerprint specimen stickers onto cards for scanning. These unique features provide an inexpensive and expedited method of handling BioSc specimens.

The system scans and saves all the print specimens directly from the media on which they are originally captured (such as paper, foam, film, etc.)

Example

Figure 7:
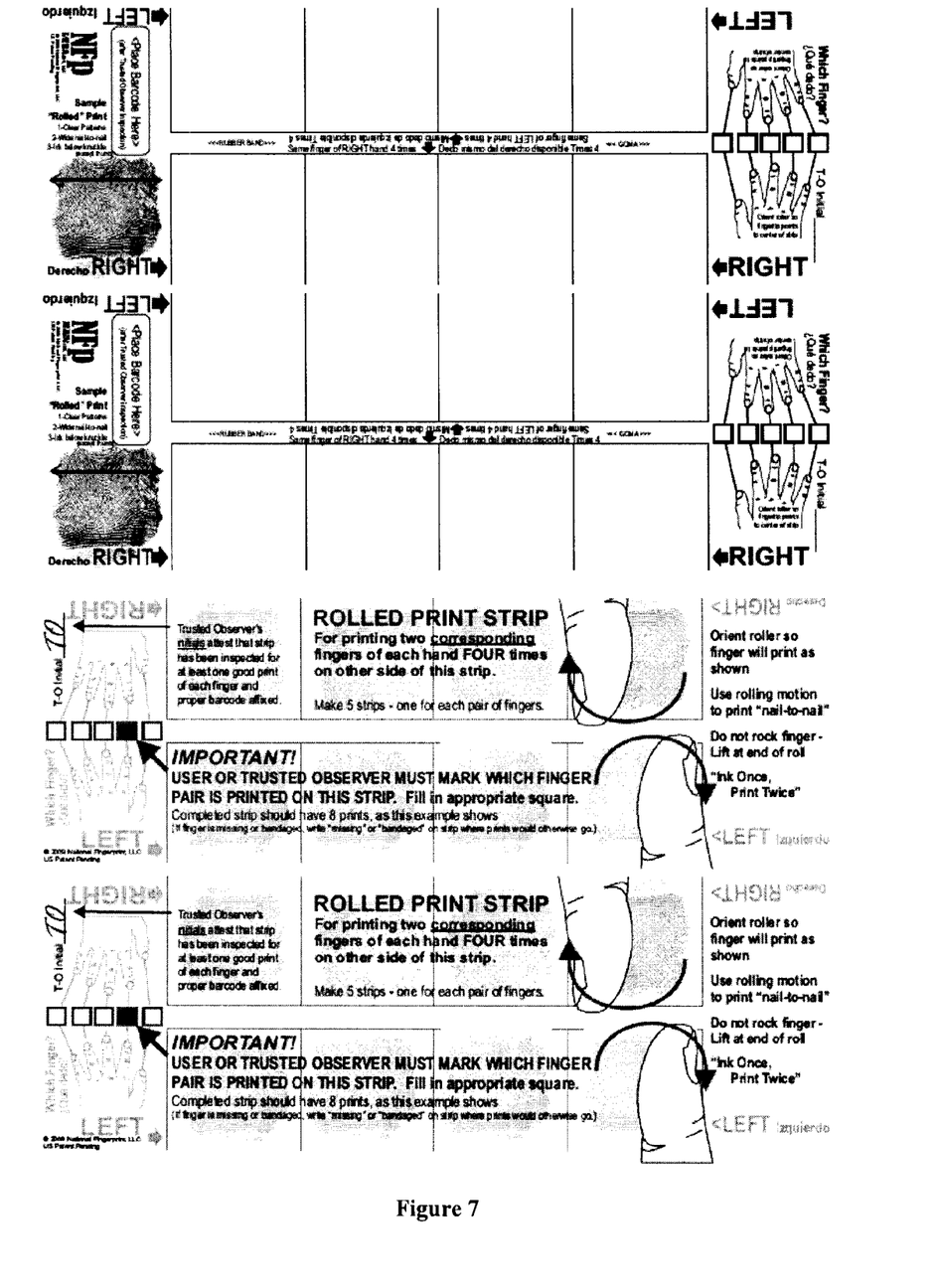
FIG. 7 is a depiction of an embodiment showing Biometric Self-capture of rolled fingerprint specimens. Rolled fingerprints are typically difficult to capture. This Figure shows the collection of multiple prints for each finger in order to provide acceptable specimens for selection.

The following example of fingerprint imaging, refer to FIG. 7, is provided for illustration of the invention:

In an embodiment a kit is used to capture fingerprints from a Subject. The kit produces five rolled specimen strips 9"×3.25" or otherwise ergonomically dimensioned, four flat specimen strips 2"×8" or otherwise ergonomically dimensioned either separately or combined into a "folio", and one demographic data capture form 3"×8" either as the top part of a standard 10-print card (similar to that shown in FIG. 3) or otherwise designed for easy use by Subjects or RTOs. The items are digitally scanned using a flat bed scanner 201. The FBI requires compliance with its EFTS (Electronic Fingerprint Transmission Specification) IQS (Image Quality Specification) for scanners. All fingerprint specimens must be scanned using scanners that comply. Existing standard scanner plate dimensions are not sufficient to accommodate the 10 specimen strips; therefore multiple scans or scanners are necessary, or the software 202 identifies and defines multiple scans to comprise a multi-page form to increase efficiency.

The software 202 of the system identifies the individual ten flat prints made by the fingers of each hand, and selects the best quality specimen of each to serve as the standard-of-comparison for that Subject. The system applies image enhancement, geometric & exposure standardization, artifact rejection, and traps-out user information printed in a special color. The software 202 of the system applies similar criteria to select the best-of-breed for each rolled print specimen to create "the exemplary standards" for that Subject. Using those standards, the system arrays the best-of-breed specimens (that have already been digitized) into proper geometric position on the virtual card 205 portrayed in memory for virtual scanning and preparation of the file. The virtual card is a replica of the one specified by the Destination AFIS 206 and prepared to meet its various standards such as those of the FBI or the state of Illinois (or Nebraska with its 1000 dpi rogue standard). The system provides a fully programmable and configurable tool that enables fully compliant ten-print card Type 4 or three-print card Type 14 scanning.

Example

Figure 5:
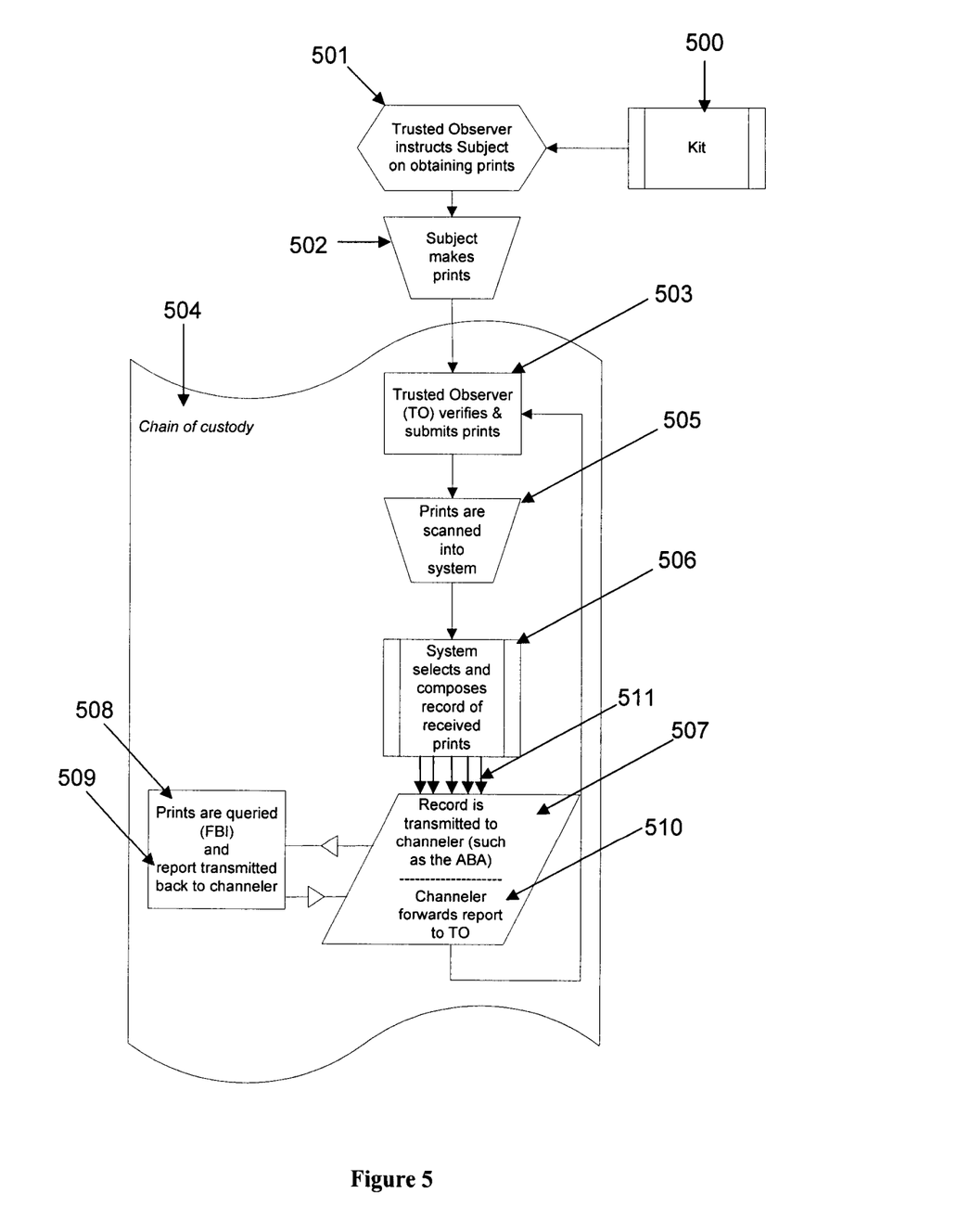
FIG. 5 is a flow chart of an embodiment of the invention.

The following example of the system is provided for illustration of the invention:

As shown in FIG. 5, a fingerprint kit 500 is forwarded to an RTO 501. The RTO (after being trained and registered) instructs a Subject as to the correct method of obtaining prints. The Subject makes prints of his/her own fingers multiple times using the claimed ergonomic device and removable media 502. The RTO verifies the quality of the fingerprint specimens confiscates and submits them under a secure chain of custody 504 to a lab 503 (such as National Fingerprint). A distinguishing and central feature of the present invention is the required use of RTOs to establish the chain of custody. In an embodiment, RTO deployment is based on use of notaries public in the United States, and their international counterparts, as capable trustworthy witnesses to the acts of Self-capture. Alternately, a human resource person or other trusted employee/consultant may be used. In an embodiment, registration is the process of recruiting and training notaries in advance or ad hoc to accomplish the required observation and attestation duty. In an example, registration is conducted in America by National Fingerprint University, a non-academic affinity group operated for National Fingerprint under direction of a trade and professional association of notaries public. By using RTOs, a chain-of-custody is created that begins when the RTO confiscates the specimens, and expires upon the official disposition of the specimens and successful upload of the data derived therefrom. Chain-of-custody is a forensic procedure to establish and maintain confidence and traceability in the integrity of evidence, and the assumption that it has not been tampered. As used in this case it refers to accountability for protecting the specimens from the point of Self-capture through any laboratory procedures and final disposition.

The prints are received at the lab and digitized by scanning the unopened transmission envelopes' barcodes 506 into the system of the invention. In addition to scanning the BioSc specimens, information assigned to the kit by the system (such as type and purpose of specimen, state or country handling or privacy rules applicable thereto, Subject, RTO, destination, etc.) is linked to the returned kit. Linking is performed by reading the barcode attached to the kit, or by any other like means, such as by an operator keying in an identifier. The barcode is read by a wand 208 (FIG. 2). The system selects the best digitized prints and composes a record of the digitized prints based on a form used by an agency 206. The record is transmitted to channeler 507 (see FIG. 5, such as the American Banker's Association) that has a connection to an agency 206 (such as the FBI). The channeler consolidates traffic flow to and from the agencies, assures privacy protection, and routes the agency report 509 (whether the prints match any in the agency database) back to the requesting entity.

Security is provided by a connection layer having multiple channels 511 that simultaneously transfer the record. The transmission is encrypted and the record is transmitted by parsing PII from the images of the biometric specimens and parsing out key identifiers such as, but not limited to a social security number and date of birth, driver's license number, and the like. The channeler has a reception module with a decryption element that receives the encrypted parsed record and reassembles it using a common key. In an embodiment, the common key is a barcode number. The record is reassembled at the channeler only after the parsed information is inside the channeler's security layer. Integrity verifiers are used to ensure that the record is reassembled intact.

The channeler forwards the report to the RTO or other authorized official 510.

Example

The following example of the image-scanning-and-processing module (as described above) is provided for illustration of the invention:

As shown in FIG. 6, the image-scanning-and-processing module 209 outputs a generic record layout containing all data fields required by any AFIS. The module accommodates plain scans (using stickers and paste-up), as well as more sophisticated or fancy scans (direct image uptake & manipulation).

A Custom Record Layout subroutine that knows files and layouts for insertion of data to form a record layout that is customized to the specs of the destination AFIS.

A Custom Batch Uploader serves as a transmission control session module. The Uploader sets up, accumulates batches, and conducts scheduled uploads as the AFIS specifies.

An Accounting & Reporting module composes and feeds transactions to a platform (such as QuickBooks® Pro, trademark of Intuit, Inc.) or any other commercial accounting platform, all of which transactions are planned, recorded, and supervised by a custom system of rules uniquely and separately claimed, called MABIL (master file, accounting, barcode, integrated, look-up). The rules include:

A) Master file: includes all of the information regarding a kit and a requestor.

B) Accounting: invoicing and charges based on requestors, agencies, etc.

C) Barcode: links kit to master file and to parsed and separately communicated PII.

D) Information: database of all clients, RTOs, requirements of agencies, states, etc.

E) Look-up: the act of relating items A)-D) via an on-line real time access method.

In an embodiment, multiple biometric specimens from a single individual are Captured and processed. A multiple specimen kit (pack) is provided for the Subject to provide specimens, such as fingerprints, palm prints, tooth bite impressions, cheek-swab DNA, saliva, scent, hair, any written list of direct linear measurements, hand-sketches, worded descriptions, descriptive locations of tattoos, piercings, other unique body observables such as missing appendages, and the like. Data from the specimens are digitally captured and complied with demographic information about the Subject. The processed information is especially useful for Subject identification in disasters.

The foregoing description of the invention has been presented for purposes of illustration and description. It is neither intended to be exhaustive nor to limit the invention to the precise form disclosed. Many alternatives, modifications, and variations will be apparent to those skilled in the art. Accordingly, this invention is intended to embrace all alternatives, modifications, and variations that fall within the spirit and broad scope of the claims.

I claim:

1. A system for deriving and compiling data from a plurality of biometric self-capture specimens and creating an electronic record of the compiled data for transmission to a secure database for subsequent processing, the system comprising: a processor interconnected to a scanner wherein the processor is configured to 1) activate the scanner to create one or more digital images of a plurality of biometric self-capture specimens provided by a subject, 2) link said one or more images to information stored in a memory of the processor, the information assigned to the specimens, 3) assign a score to individual components of said one or more images based on quality according to a standard for that component, wherein each component is a digital representation of a specimen and at least some of the components represent duplicative specimens, 4) display the scores to a user, 5) retain the components with the highest scores, 6) arrange the retained components and the linked information in a predetermined format to create an electronic record and 7) transmit the electronic record to a secure database in a secure manner.

2. The system of claim 1 wherein the system is configured to transmit the electronic record to the secure database via a channeler.

3. The system of claim 1 wherein the system is configured to encrypt the electronic record and transmit the electronic record through a connection layer with multiple channels that simultaneously transfer data.

4. The system of claim 1 wherein the system is configured to parse Personally Identifiable Information in the electronic record from the digital images of the biometric specimens prior to transmitting the electronic record to a secure database.

5. The system of claim 4 wherein the Personally Identifiable Information comprises at least one of social security number, date of birth, driver's license number, vehicle registration plate number, credit card numbers, birthday and birthplace.

6. The system of claim 4 wherein the system is configured to transmit the electronic record to a secure database which comprises a reception module having a decryption element that receives the encrypted parsed record and reassembles it using a common key.

7. The system of claim 6 wherein the common key is a barcode number.

8. The system of claim 1 wherein the plurality of specimens is a plurality of fingerprints specimens, and each of the components scored by the system is a digital representation of one of the plurality of fingerprint specimens.

9. A computer-implemented method of deriving and compiling data from a plurality of biometric self-capture specimens to create an electronic record of the compiled data to be used for subsequent processing, the method comprising:
   1) activating a scanner to create one or more digital images of a plurality of biometric self-capture specimens provided by a subject,
   2) linking said one or more images to information stored in a memory of a processor, the information assigned to the specimens,
   3) enhancing said one or more images and assigning a score to individual components of said one or more images based on quality according to a standard for that component,
   4) displaying the scores to a user,
   5) retaining the components with the highest scores, and
   6) arranging the retained components and the linked information to create an electronic record comprising the retained components and linked information in a predetermined format, wherein the plurality of specimens comprises a plurality of fingerprint specimens, and each of the scored components is digital representation of one of said plurality of fingerprint specimens.

10. The method of claim 9 further comprising the step of transmitting the electronic record to a channeler for subsequent transmission to a secure database in a secure manner.

11. The system of claim 8, wherein each of the retained components are non-duplicative digital representations of fingerprint specimens, and the electronic record comprises a virtual fingerprint card having the retained components in a predetermined arrangement.

12. The system of claim 11, wherein the electronic record comprises a virtual fingerprint card having digital representations of the fingerprint of each finger of a subject.

13. The system of claim 12, wherein the virtual fingerprint card includes digital representations of a rolled fingerprint specimen of each finger of a subject, a plurality of non-duplicative digital representations of flat fingerprint specimens of the subject, and demographic information about the subject.

14. The method of claim 9, wherein at least some of the fingerprint specimens are scanned a plurality of times, and further wherein the step of retaining the components with the highest scores comprises comparing the scores of image components representing repeated scans of the same fingerprint specimen and retaining the image component of that fingerprint specimen having the highest score.

15. The method of claim 9, wherein at least some of the fingerprint specimens comprise repeated captures of the same fingerprint by a subject, and further wherein the step of retaining the components with the highest scores comprises comparing the scores of image components representing repeated captures of the same fingerprint and retaining the image component of that fingerprint having the highest score.

16. The method of claim 15, wherein each of the retained components are non-duplicative digital representations of fingerprint specimens, and the electronic record comprises a virtual fingerprint card having the retained components in a predetermined arrangement.

17. The method of claim 16, wherein the electronic record comprises a virtual fingerprint card having digital representations of the fingerprint of each finger of a subject.

18. The system of claim 17, wherein the virtual fingerprint card includes digital representations of a rolled fingerprint specimen of each finger of a subject, a plurality of non-duplicative digital representations of flat fingerprint specimens of the subject, and demographic information about the subject.

* * * * *